United States Patent [19]
Sato et al.

[11] Patent Number: 5,897,993
[45] Date of Patent: Apr. 27, 1999

[54] METHOD OF DETERMINING THE NUMBER OF BACTERIA QUICKLY AND A DEVICE FOR DETERMINING THE NUMBER OF BACTERIA

[75] Inventors: Mikio Sato, Ichihara; Tomomi Ito, Sodegaura, both of Japan

[73] Assignee: Idemitsu Kosan Company Limited, Tokyo, Japan

[21] Appl. No.: 08/894,820

[22] PCT Filed: Mar. 28, 1996

[86] PCT No.: PCT/JP96/00815

§ 371 Date: Aug. 29, 1997

§ 102(e) Date: Aug. 29, 1997

[87] PCT Pub. No.: WO96/30542

PCT Pub. Date: Oct. 3, 1996

[30] Foreign Application Priority Data

Mar. 28, 1995 [JP] Japan .................................. 7-093184
Aug. 9, 1995 [JP] Japan .................................. 7-222728
Aug. 30, 1995 [JP] Japan .................................. 7-243841

[51] Int. Cl.$^6$ .............. C12Q 1/02; C12Q 1/62; C12Q 1/54; G01N 33/53
[52] U.S. Cl. .............. 435/29; 435/10; 435/12; 435/14; 435/4; 435/34; 435/968; 435/283.1; 435/287.4; 435/975; 435/287.1
[58] Field of Search .................. 435/29, 10, 12, 435/14, 4, 34, 968, 283.1, 287.4, 975, 287.1; 422/50, 52, 68.1

[56] References Cited

U.S. PATENT DOCUMENTS 5,403,720  4/1995  Sato et al. ................................. 435/29

FOREIGN PATENT DOCUMENTS 0 465 987 A2  1/1992  European Pat. Off. .
57-74095      5/1982  Japan .
62-138185     6/1987  Japan .
1-124767      5/1989  Japan .
3-27636       1/1991  Japan .

OTHER PUBLICATIONS

Edited by Kyoto University Rokuseikai, "New edit. Agricultural Chemistry experiment Book", vol. 2, Apr. 10, 1957, pp. 428–429 Sangyo Tosho (Tokyo).

*Primary Examiner*—Louise N. Leary
*Attorney, Agent, or Firm*—Frishauf, Holtz, Goodman, Langer & Chick, P.C.

[57] ABSTRACT

A method of determining the number of bacteria in a sample which involves introducing a sample containing bacteria into a tubular filtering vessel holding therein a hydrophobic filter for bacterial detection, a coloring composition is disposed on the side of the filter where the sample is introduced into the vessel, and a support for the filter is disposed on the opposite side of the filter from the coloring composition. The bacteria is subjected to and the sample is filtered dyeing sample by suction from the support to collect the dyed bacteria on the filter and remove the excess of coloring matter. The number of the bacteria in the sample is determined from the degree of staining of the filter.

29 Claims, 4 Drawing Sheets

METHOD OF DETERMINING THE NUMBER OF BACTERIA QUICKLY AND A DEVICE FOR DETERMINING THE NUMBER OF BACTERIA

TECHNICAL FIELD

This invention relates to a method and a device which make it possible to determine the number of bacteria in a sample quickly and easily in a single step of filtering operation without requiring any highly developed skill, or expert knowledge.

This invention further relates to a method and a kit which make it possible to determine the number of bacteria in a sample quickly and easily in a single step of filtering operation without requiring any highly developed skill, or expert knowledge, since no dropper, or other device is required for taking a sample to be inspected, but a filtering operation under suction with a syringe is sufficient therefore.

This invention can be used effectively in a wide variety of fields, such as the field of diagnosis based on bacteria in urine, the field of metal processing fluids, the field of dyes involving a problem of decomposition, the field of food, and the field of environmental problems including that of hot-spring water.

BACKGROUND ART

In the field of urine analysis, etc., it has been usual to determine the number of bacteria, etc. in a sample of urine, etc. to discover inflammation and estimate the condition of a disease.

For example, a case involving an increase of bacteria in urine is diagnosed as bacteriuria, and suggests an infection of the urinary tract. Accordingly, the number of bacteria is determined for early treatment and administration of medicine.

In the field of food, etc., the number of bacteria, etc. in food are determined to see if it has not been decomposed, and in the case of fermented milk, lactic-acid beverages, etc., the determination of the number of lactic-acid bacteria in the food is performed to control it.

The determination of the number of bacteria in such cases is mainly performed by a method employing agar plate culture.

This method, however, requires expert skill and an apparatus called an incubator, and calls for 24 to 48 hours to give results.

In the case of urine analysis, for example, it is after several days that a doctor knows the results of an examination by culture of an outpatient's sample of urine which is performed in a bacteriological examination room, or center. A method for the quick determination of bacteria is desired for diagnosis of high accuracy.

Food is examined for *Escherichia coli* and for general bacteria, and while the results of an examination for *Escherichia coli* are available from 18 hours of culture, an examination for general bacteria requires 24 or more hours of culture, and the results thereof are usually available for many foods only after their shipment. An improvement has been desired for bacterial control in the determination of, among others, the number of lactic-acid bacteria in fermented milk, etc., since it usually requires about 72 hours of culture, and the number of lactic-acid bacteria is known only after the shipment of commercial products, and in many cases after consumers have drunk or eaten the products.

In the field of metal processing fluids, such as water-soluble cutting fluids, the growth of bacteria is likely to cause the decomposition of fluids. An easy culture kit (such as one sold under the tradename, "Easicult") is presently available for checking the presence of bacteria, but takes 48 hours to give results. Therefore, it is likely that the measures taken for preventing decomposition may be too late to prevent any objectionable odor from being produced by decomposition.

Moreover, there have been proposed a method of determining the enzyme activity of bacteria (Japanese Patent Application Laid-Open No. Sho 57-74095), a method using a fluorescent dye (Japanese Patent Application Laid-Open No. Sho 62-138185), a filter dyeing method (Japanese Patent Application Laid-Open No. Hei 1-124767), etc; though they are not presently employed in practice, but they have revealed drawbacks, such as the instability of a reagent used for determining enzyme activity, the necessity for a special apparatus (fluorophotometer), and the complicated operation involved in the dyeing process.

The applicant of this application has already proposed a method for determining the number of microorganisms in a sample by either dyeing the microorganisms and collecting them in a hydrophobic filter, or collecting them in a hydrophobic filter and dyeing them, washing away the excess of coloring matter and determining the number of the microorganisms in the sample from the degree of their staining, as a method overcoming the drawbacks of the prior art as stated above (Japanese Patent Application Laid-Open No. Hei 4-218392).

This method has made it possible to determine the number of microorganisms in a sample quickly and easily without requiring any highly developed skill, expert knowledge, or special equipment.

The actual use of the method has, however, revealed that it is difficult and complicated, since it requires two steps of filtering operation.

The necessity for the use of a dropper, or like device for taking a sample has also complicated the method.

It is an object of this invention to overcome the drawbacks of the prior art as stated above, and provide a method and a device which make it possible to determine the number of bacteria in a sample quickly (within one minute) and easily in a single step of filtering operation without requiring any special equipment, or expert knowledge.

It is a further object of this invention to provide a method and a kit which make it possible to determine the number of bacteria in a sample quickly (within one minute) and easily in a single step of filtering operation without requiring any special equipment, or expert knowledge, since no dropper, or like device is used for taking a sample, but a filtering operation under suction with a syringe is sufficient therefore.

DISCLOSURE OF THE INVENTION

A first embodiment of the invention provides a method of determining the number of bacteria in a sample quickly which comprises introducing a sample containing bacteria into a tubular filtering vessel holding therein a hydrophobic filter for bacterial detection, a coloring composition on that side of the filter where the sample is introduced into the vessel, and a support for the filter on the opposite side of the filter from the coloring composition, dyeing the bacteria, filtering the sample by suction from the support to collect the dyed bacteria on the filter and remove the excess of coloring matter, and determining the number of the bacteria in the sample from the degree of staining of the filter.

A second embodiment of the invention provides a method of determining the number of bacteria in a sample quickly which comprises introducing a sample containing bacteria into a tubular filtering vessel holding therein a hydrophobic filter for bacterial detection, a coloring composition on that side of the filter where the sample is introduced into the vessel, and a support for the filter, a piston and an aqueous solution on the opposite side of the filter from the coloring composition, dyeing the bacteria, filtering the sample by moving the piston in the aqueous solution in the vessel to collect the dyed bacteria on the filter and remove the excess of coloring matter, and determining the number of the bacteria in the sample from the degree of staining of the filter.

The second embodiment of the invention is characterized by including the piston and the aqueous solution in the filtering vessel according to the first embodiment of the invention.

A third embodiment of the invention provides a device for determining the number of bacteria which comprises a tubular filtering vessel having a sample inlet at one end, while the other end thereof enables suction with a syringe, the vessel holding a coloring composition, a hydrophobic filter for bacterial detection and a filter support therein in their order as viewed from the sample inlet.

A fourth embodiment of the invention provides a device for determining the number of bacteria which comprises a tubular filtering vessel having a slender sample introducing tube connected at one end, while the other end thereof enables suction with a syringe, the vessel holding a prefilter, a coloring composition, a hydrophobic filter for bacterial detection, a filter support, a piston movable in the vessel, an aqueous solution and a plug preventing the leakage of the aqueous solution therein in their order as viewed from the slender tube.

The fourth embodiment of the invention is characterized by including the prefilter, piston movable in the vessel, aqueous solution, and plug preventing the leakage of the aqueous solution in the filtering vessel according to the third embodiment of the invention.

The fifth embodiment of the invention provides a method of determining the number of bacteria in a sample quickly which comprises introducing a sample containing bacteria by suction into a filtering vessel holding a hydrophobic filter for bacterial detection therein, extruding it into a coloring composition, filtering it by suction to collect the dyed bacteria on the filter and determining the number of the bacteria in the sample from the degree of staining of the filter.

The sixth embodiment of the invention provides a kit for determining the number of bacteria which comprises a filtering vessel holding a hydrophobic filter for bacterial detection and a filter support therein, a sampling member containing a prefilter and adapted for connection to one end of the vessel, a coloring composition, a vessel for the coloring composition and a color reference chart.

The seventh embodiment of the invention provides a kit for determining the number of bacteria which comprises a filtering vessel holding a hydrophobic filter for bacterial detection and a filter support therein, a sampling member adapted for connection to one end of the vessel, a coloring composition, a vessel for the coloring composition and a color reference chart.

The seventh embodiment of the invention differs from the sixth embodiment of the invention in that the sampling member does not contain any prefilter.

BRIEF DESCRIPTION OF THE DRAWINGS

In FIGS. 1 to 4, symbol A denotes a filtering vessel, symbol 1 a slender sampling tube, symbol 2 a sampling scale, symbol 3 a severing mark, symbol 4 a prefilter, symbol 5 a coloring composition, symbol 6 a hydrophobic filter for bacterial detection, symbol 7 a filter support, symbol 8 a piston, symbol 9 an aqueous solution, symbol 10 a tubular insert, symbol 11 a tubular insert, symbol 12 a plug, symbol 13 a syringe, symbol 14 a plunger, symbol 15 a sample inlet, and symbol 16 a plug.

In FIGS. 5 and 6, symbol A denotes a filtering vessel, symbol B a syringe, symbol C a sampling member, symbol D a coloring composition, symbol E a vessel for the coloring composition, symbol F a color reference chart, symbol 21 a hydrophobic filter for bacterial detection, symbol 22 a filter support, symbol 23 a prefilter, symbol 24 a sample inlet, symbol 25 a dropping bottle, and symbol 26 a piston.

BEST MODE OF CARRYING OUT THE INVENTION

Figure 1:
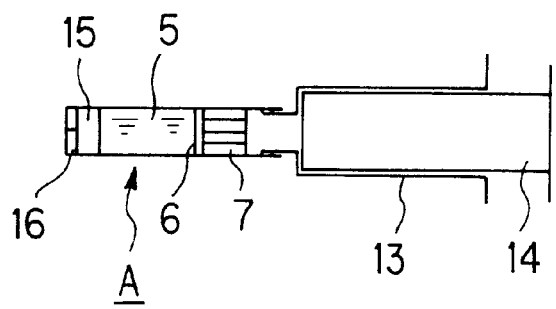
FIG. 1 is an schematic view showing one form of a device of the third embodiment of the invention for determining the number of bacteria.

The first embodiment of the invention and the fifth embodiment of the invention are basically different from each other in whether the coloring composition is held in the filtering vessel, or not.

The method of the first embodiment of the invention is preferably carried out by employing the device of the third embodiment of the invention. The method of the second embodiment of the invention is preferably carried out by employing the device of the fourth embodiment of the invention.

Therefore, description will now be made of the method of the first embodiment of the invention with reference to the device of the third embodiment of the invention, and then of the method of the second embodiment of the invention with reference to the device of the fourth embodiment of the invention.

Referring first to the method of the first embodiment of the invention, a sample containing bacteria (for example, fermented milk, or a lactic-acid beverage) is introduced into a tubular filtering vessel holding therein a hydrophobic filter for bacterial detection, a coloring composition on that side of the filter where the sample is introduced (on the left-hand side of the filter in FIG. 1 as will be described) and a support for the filter on the opposite side of the filter from the coloring composition (on the right-hand side of the filter in FIG. 1 as will be described), and is dyed before the number of bacteria in the sample is determined.

The filtering vessel is tubular, or may be cylindrical or tubular, and may be of either plastics, such as vinyl chloride, or glass. Its capacity depends on the amount of the coloring composition, etc. as employed.

The filtering vessel holds therein a hydrophobic filter, a coloring composition on that side of the filter where the sample is introduced, and a support for the filter on the opposite side of the filter from the coloring composition. The filtering vessel is preferably according to the third embodiment of this invention.

Referring now to the method of the second embodiment of the invention, a sample containing bacteria is introduced into a tubular filtering vessel holding therein a hydrophobic filter for bacterial detection, a coloring composition on that side of the filter where the sample is introduced (on the left-hand side of the filter in FIG. 2 as will be described) and a support for the filter, a piston and an aqueous solution on the opposite side of the filter from the coloring composition (on the right-hand side of the filter in FIG. 2 as will be described), and is dyed before the number of bacteria in the sample is determined.

The filtering vessel according to the second embodiment of the invention is tubular, or may be cylindrical or tubular, and may be of either plastics, such as vinyl chloride, or glass, as is the case with the first embodiment of the invention. Its capacity depends on the amount of the coloring composition, etc. as employed. The filtering vessel holds therein a hydrophobic filter for bacterial detection, a coloring composition on that side of the filter where the sample is introduced, and a support for the filter, a piston and an aqueous solution on the opposite side of the filter from the coloring composition. The filtering vessel is preferably according to the fourth embodiment of the invention.

The invention will now be described with reference to the drawings. FIG. 1 is an explanatory view showing one form of a device of the third embodiment of the invention for determining the number of bacteria. In the drawing, symbol A denotes a filtering vessel.

The filtering vessel A in the device of the third embodiment of the invention for determining the number of bacteria is a tubular one having a sample inlet 15 at one end, while the other end thereof enables suction with a syringe 13, and the filtering vessel A holds a coloring composition 5, a hydrophobic filter 6 for bacterial detection and a filter support 7 therein in their order as viewed from the sample inlet 15. The syringe 13 can be included in the device of the third embodiment of the invention, if required.

The sample inlet 15 at one end of the filtering vessel A has an end which may be left open, or may be provided with an appropriate plug 16 for preventing the leakage of the coloring composition 5. The plug 16 may be replaced by a tubular insert, or the like.

The other end of the filtering vessel A enables suction with the syringe 13 which can be connected thereto at one end. The syringe 13 itself can, however, be included in the device of this invention, if required, as stated above.

The coloring composition 5 held in the filtering vessel A is a composition which can be used for both dyeing and washing, and more specifically, it comprises coloring matter which can be used for dyeing bacteria, and water, or a buffer solution.

Examples of the coloring matter which can be used for dyeing bacteria are Safranine, Fuchsine, Methylene Blue, Methyl Green, Crystal Violet, Gentiana Violet and Victoria Blue B, and Safranine, Fuchsine, Methylene Blue or Methyl Green is preferred from the standpoint of easy judgment.

The buffer solution which can be used has a pH of 4 to 9 and preferably has a pH of 5 to 7 to ensure the stability of the coloring matter. A preservative, such as ethanol, a surface active agent, etc. can be added, if required.

The concentration of the coloring matter is usually from 0.00001 to 0.00045% (w/v) and preferably from 0.00015 to 0.0004% (w/v) when it is Fuchsine. If its concentration is less than 0.00001%, it is insufficient for any satisfactory coloring, and if its concentration exceeds 0.00045%, it is difficult to remove any excess of the coloring matter.

If it is necessary to add a preservative, such as ethanol, it can be added in the amount of 0.1 to 15% (w/v), and if a surface active agent is added, it can be added in the proportion of from 0.001 to 1.0% (w/v), and preferably from 0.01 to 0.6% (w/v).

The adequate amount of the coloring composition to be used per sample is two to five times the amount of the sample. The amount of each sample is usually 50 to 100 $\mu$l. Therefore, any sample in the amount of 100 $\mu$l requires 200 to 500 $\mu$l of coloring composition. No amount exceeding five times that of the sample is, however, required.

It is preferable for preventing any error to use the same amount of the coloring composition when preparing a color reference chart or a working curve as when applying it to any sample containing an unknown number of bacteria.

The filtering vessel A holds the hydrophobic filter 6 for bacterial detection after the coloring composition 5 as viewed from the sample inlet 15. The method of this invention employs a hydrophobic filter 6 as a filter for bacterial detection. The hydrophobic filter is suitable as a filter for collecting bacteria, since it is of low or no polarity, and it is easy to remove any excess of coloring matter therefrom. A polar filter is undesirable, as it is not easy to remove any excess of coloring matter therefrom.

The hydrophobic filter 6 is of, for example, any of nylons, fluororesins such as polytetrafluoroethylene, polyolefins such as polypropylene, polycarbonates, and glass. A hydrophobic filter made of polytetrafluoroethylene or polypropylene is, among others, preferred, as it is easy to remove any excess of coloring matter.

A filter of a hydrophilic material, such as nitrocellulose, can be used as a hydrophobic filter if its surface is made hydrophobic by surface treatment. Its surface treatment is, for example, its coating with any of the materials including nylons, fluororesins and polyolefins as mentioned above.

The hydrophobic filter 6 for bacterial detection has a pore diameter of, say, 0.2 to 3.0 $\mu$m which is usually adopted for a filter for collecting bacteria.

The hydrophobic filter 6 has an area of filtration by suction (a coloring zone) which is not particularly limited in size if it is easily visible. The coloring zone is not particularly limited in shape, but in order to be easily visible, it is preferably circular with a diameter of, say, 1 to 3 mm. There is no particular limitation in the size of the hydrophobic filter 6 as a whole, either, though it is at least equal to the size of the coloring zone.

The hydrophobic filter 6 may have a color so selected as to facilitate judgment by taking into consideration the coloring composition to be used. A white hydrophobic filter is preferred to facilitate judgment on the degree of coloring. A transparent or semi-transparent hydrophobic filter can also be employed, and can be placed on white paper to facilitate judgment.

The filtering vessel A holds the filter support 7 after the coloring composition 5 and the hydrophobic filter 6 for bacterial detection as viewed from the sample inlet 15. The filter support 7 may be of any material and shape if it can support the hydrophobic filter 6. It is usually formed from a silicone resin, or the like.

The filtering vessel A in the device for determining the number of bacteria is a tubular one having the sample inlet 15 at one end, while the other end thereof enables suction with the syringe 13, as stated above, and the filtering vessel A holds the coloring composition 5, the hydrophobic filter 6 for bacterial detection and the filter support 7 therein in their order as viewed from the sample inlet 15.

The device of this invention for determining the number of bacteria of the third embodiment of the invention has a construction as described above.

According to the method of the first embodiment of the invention, an appropriate sample containing bacteria, preferably such as fermented milk, or a lactic-acid beverage, is introduced into the filtering vessel A, and dyed.

There is no particular limitation to the sample to which this invention is applicable, but it is applicable to a wide variety of samples including not only urine, but also water-soluble metal processing fluids such as cutting, rolling and heat-treatment fluids, liquid foods such as liquid seasonings (soy, sauce, etc.), liquid foods and beverages (fermented milk, lactic-acid beverages, etc.) and alcoholic drinks (wine, sake, etc.), samples left after washing powdery, or solid foods (vegetables, fish, meat, etc.), water-soluble paints, and water, such as river, pond or hot-spring water, water in a water tank, or waste water from houses. The sample can be appropriately diluted as required, or can be crushed and diluted if it is of, for example, a solid food.

The method as set forth in claim 1 is intended for determining quickly the total number of bacteria existing in any such sample, for example, *Escherichia coli, Staphylococcus aureus* and *Pseudomonas aeruginosa*.

The first and third embodiments of the invention are particularly useful for determining the number of lactic-acid bacteria in fermented milk and lactic-acid beverages quickly.

Description will now be made of the process in which a sample containing bacteria as mentioned above is placed in the filtering vessel A, and dyed in accordance with the first embodiment of the invention.

The syringe 13 is attached to the opposite end of the filtering vessel A from its sample inlet 15 (though this step is unnecessary if the syringe is already set in position), and a sample containing bacteria is introduced through the sample inlet 15, and dyed.

More specifically, the sample is dropped into the coloring composition 5 through the sample inlet 15 by means of, for example, a dropper, and is thoroughly mixed with the coloring composition 5, and thereby dyed. If the plug 16 exists adjacent to the sample inlet 15, the plug 16 is removed before the sample is dropped into the coloring composition 5 by means of a dropper, or the like. If an inserted tube exists instead of the plug 16 adjacent to the sample inlet, a dropper can advantageously be passed through the center of the tube to drop the sample into the coloring composition 5.

Then, the plunger 14 of the syringe 13 is pulled to cause filtration by suction (by drawing air through the filter support 7), whereby the collection of the dyed bacteria on the hydrophobic filter 6 and the removal of any excess of coloring matter are simultaneously carried out. The suction caused by pulling the plunger 14 of the syringe 13 enables a solution containing the sample as dyed (a mixture of the sample and the coloring composition 5) to be collected on the hydrophobic filter 6 simultaneously with the removal of the excess of coloring matter.

As it enables the collection of the dyed bacteria on the hydrophobic filter and the removal of the excess of coloring matter to be carried out simultaneously, the method of the first embodiment of the invention is a simple process.

According to the method of the first embodiment of the invention, the collection of the dyed bacteria on the hydrophobic filter and the removal of the excess of coloring matter are carried out simultaneously, as described, for determining the number of the bacteria in the sample from the degree of staining on the filter.

The number of bacteria in the sample is determined from the degree of staining of the bacteria in the sample from which the excess of coloring matter has been removed, as stated above.

For determining the number of bacteria, (1) the simplest way is a visual comparison with a color reference chart, but (2) it is also possible to employ colorimetric analysis by measuring optical density. Visual judgment can be made by examining the degree of staining not only on the front side of the hydrophobic filter, but also on its rear side. For this purpose, it is possible to prepare for each side a color reference chart and a working curve showing absorbance and the number of bacteria.

The visual determination of the number of bacteria as stated at (1) above can more specifically be carried out by comparing the degree of staining of bacteria on the hydrophobic filter, or the intensity of their color with a color reference chart prepared by employing samples containing known numbers of bacteria.

The color reference chart can be prepared by taking color photographs of a hydrophobic filter dyed and washed by employing samples containing know numbers of bacteria in accordance with the method of the first embodiment of the invention, or by coloring filter paper, or the like to the same degree with any such dyed filter, or by printing colors of the same degree on paper.

The following is a description of a color reference chart which is prepared for determining the number of bacteria in urine. Although even the urine of a healthy person contains bacteria at a low concentration [at most about 10,000 per ml (milliliter)], the presence of 100,000 or more per ml is suspected as a case of bacteriuria, and the presence of 1,000,000 or more per ml is definitely concluded as a case of a bacterial infection (bacteriuria). It is, therefore, useful to prepare a color reference chart which enables determination in the vicinity of these values. It is usually sufficient to prepare a standard color reference chart for five levels, i.e., 1,000 per ml, 10,000 per ml, 100,000 per ml, 1,000,000 per ml and 10,000,000 per ml, though this is not intended to be limitative.

The calorimetric analysis based on optical density (O.D.) as stated at (2) above may be carried out by dissolving in an organic solvent the coloring matter which has stained the bacteria on the hydrophobic filter, determining the degree of staining of the resulting solution from its absorbance and comparing it with a working curve prepared beforehand and showing optical density (O.D.) and the number of bacteria. The wavelength employed for measuring absorbance depends on the coloring matter used. Any alcohol can be used as the organic solvent, but ethanol is, among others, preferred.

A working curve can be prepared as will now be stated by way of example. The degrees of staining of diluted samples having different concentrations are determined by using a microplate reader as optical density (O.D.) at 492 nm if Fuchsine is used as coloring matter, while the numbers of bacteria in the solutions of the same samples as the diluted ones are obtained by counting the number of colonies grown by agar plate culture, and the results of both are combined to form a working curve showing the number of bacteria and optical density.

The second embodiment of the invention will now be described based on the drawings and with reference to the fourth embodiment of the invention.

Figure 2:
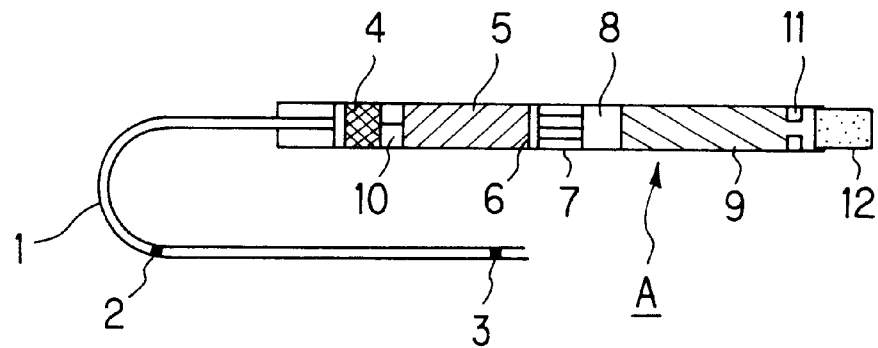
FIG. 2 is an schematic view showing one form of a device of the fourth embodiment of the invention for determining the number of bacteria.
Figure 3:
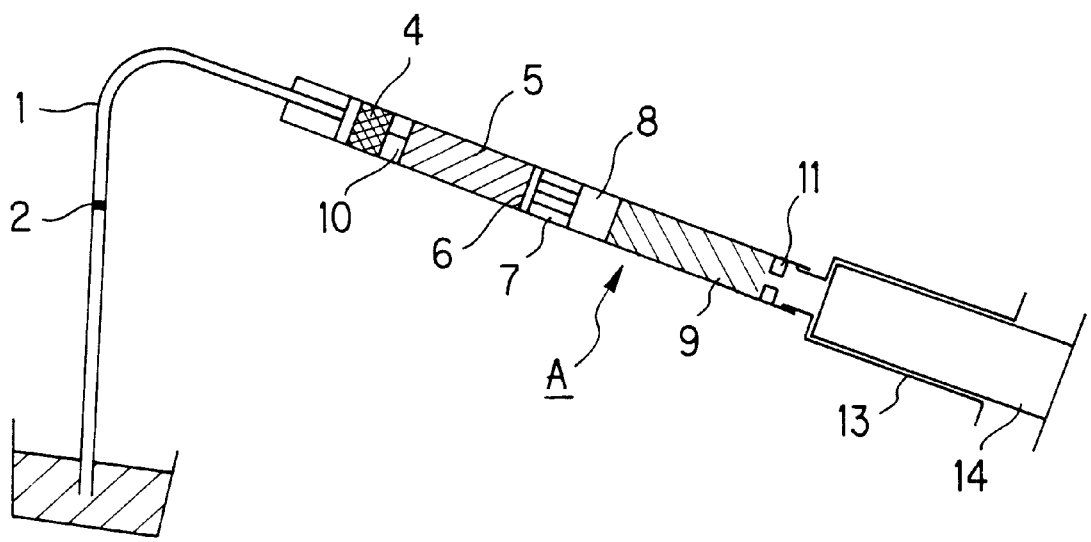
FIG. 3 is an schematic view showing the mode in which a sample is introduced into the device of this invention for determining the number of bacteria shown in FIG. 2 by a syringe attached thereto.

FIG. 2 is a schematic view showing one form of a device representing the fourth embodiment of the invention for determining the number of bacteria. FIG. 3 is an explanatory view showing the mode in which a sample is introduced into the device shown in FIG. 2 by a syringe attached thereto. FIG. 4 (FIGS. 4(a) to (f)) shows the manner in which the device is used. In the drawings, symbol A denotes a filtering vessel.

The filtering vessel A in the device for determining the number of bacteria of the fourth embodiment of the invention is a tubular one having a slender sampling tube 1 attached to one end thereof, while the other end thereof enables suction with a syringe 13, and the filtering vessel A holds a prefilter 49 a coloring composition 5, a hydrophobic filter 6 for bacterial detection, a filter support 7, a piston 8 movable in the filtering vessel, an aqueous solution 9 and a plug 12 for preventing the leakage of the aqueous solution therein in their order as viewed from the slender tube 1. The syringe 13 can be included in the device of this invention, if required.

The slender sampling tube 1 attached to one end of the filtering vessel A is formed from a flexible material, for example, a polyethylene, or like resin, and usually has a sampling scale 2 marked in its mid-portion for showing a standard amount of a sample. The scale may cover a range of 50 to 100 $\mu$l which is the amount of a sample which is usually employed. The slender sampling tube 1 has a distal end which is usually closed to avoid contamination, though it may alternatively be left open, and which is preferably provided with a severing mark 3, as shown.

The other end of the filtering vessel A enables suction with the syringe 13 which can be connected thereto at one end. The syringe 13 itself can, however, be included in the device of the fourth embodiment of the invention, if required, as stated above.

The filtering vessel A first holds the prefilter 4 as viewed from the slender tube 1. The prefilter 4 is used for removing animal cells, and if a sample contains animal cells larger than bacteria, for example, leukocytes, it does not pass any such cells, but collects them, while passing bacteria. The prefilter 4 may have a pore diameter of, say, 6 to 8 microns. It is possible to use as the prefilter a polypropylene filter (having a pore diameter of, say, 7 microns), a urine sampling filter (made of vinyl chloride) for a medicine for a diagnosis for pregnancy, such as "Gonavislide" and "New Gonavislide" (products of Mochida Pharmaceutical Co., Ltd.) which will appear in the description of examples, a felt, or non-woven fabric used in a commercially available oily-ink pen, or the like.

The filtering vessel A holds the coloring composition 5 after the prefilter 4 as viewed from the slender tube 1. A tubular insert 10 is usually disposed between the prefilter 4 and the coloring composition 5 for avoiding their contact. The tubular insert 10 is formed from a synthetic resin, such as a silicone resin, and is provided for preventing any contact between the prefilter 4 and the coloring composition 5 prior to use, though it allows a sample containing bacteria to be drawn into the coloring composition 5 through the prefilter 4 upon suction with the syringe.

The filtering vessel A holds the hydrophobic filter 6 for bacterial detection after the prefilter 4 and the coloring composition 5 as viewed from the slender tube 1. The hydrophobic filter 6 duplicates that which has been described in the description of the first and third embodiment of the invention.

The filtering vessel A holds the filter support 7, piston 8 movable in the filtering vessel, aqueous solution 9, and plug 12 for preventing the leakage of the aqueous solution in their order after the prefilter 4, coloring composition 5, and hydrophobic filter 6 as viewed from the slender tube 1.

The filter support 7 may be of any material and shape if it can support the hydrophobic filter 6. It is usually formed from a silicone resin, or the like.

The piston 8 movable in the filtering vessel has an outside diameter slightly smaller than the inside diameter of the filtering vessel A, and is slidable in the filtering vessel A as a result of suction, or pressure application with the syringe 13. Although the material of the piston 8 is not particularly limited, a polyacrylamide gel, or konjak (devil's-tongue) is, for example, preferred because of its light weight and low cost.

The aqueous solution 9, as well as the piston 8, isolates the syringe 13 to prevent any sample from entering the syringe 13 and protect the syringe 13 from any bacterial contamination. Accordingly, it is usually possible to use, for example, water, or an aqueous solution containing alcohol. The amount of the aqueous solution is usually, say, 500 to 1000 $\mu$l, though it depends on the shape and size of the filtering vessel, the amount of the dyeing solution, etc.

The plug 12 for preventing the leakage of the aqueous solution 9 is held at that end of the filtering vessel A to which the syringe 13 can be attached, and the plug 12 is removed when the syringe 13 is attached, as shown in FIG. 3. The plug 12 may be of any material and shape if it functions as a plug for preventing the leakage of the aqueous solution 9.

A tubular insert 11 is usually held inwardly of the plug 12 to ensure the effective avoidance of any leakage of the aqueous solution 9. The tubular insert 11 is formed from a synthetic resin, such as a silicone resin, like the tubular insert 10 as described above, and effectively prevents any leakage of the aqueous solution 9 when the plug 12 has been removed. The filtering vessel A in the device of the fourth embodiment of the invention for determining the number of bacteria is of the construction as described above.

According to the method of the second embodiment of the invention, a sample containing bacteria is introduced into the filtering vessel A, and dyed.

The second embodiment of the invention is applicable to any samples not particularly limited, but including those stated in the description of the first embodiment of the invention. The method of the first embodiment of the invention and the device of the third embodiment of the invention are simpler, and more suitable for determining the number of lactic-acid bacteria in fermented milk.

Description will now be made with reference to FIG. 4 of the process in which a sample containing bacteria as mentioned above is placed in the filtering vessel A, and dyed.

Figure 4A:
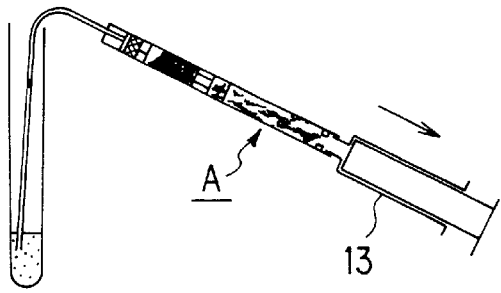
FIGS. 4(a) to (f) shows the manner in which the device of this invention for determining the number of bacteria is used.

The syringe 13 is attached to the opposite end of the filtering vessel A from the sampling tube 1 (though this step is unnecessary if the syringe is already set in position), and after the sampling tube 1 has had its distal end cut off at the severing mark 3, the filtering vessel A is lowered from its horizontal position at its end connected to the syringe 13 to take a sample, as shown in FIG. 4(a).

Figure 4D:
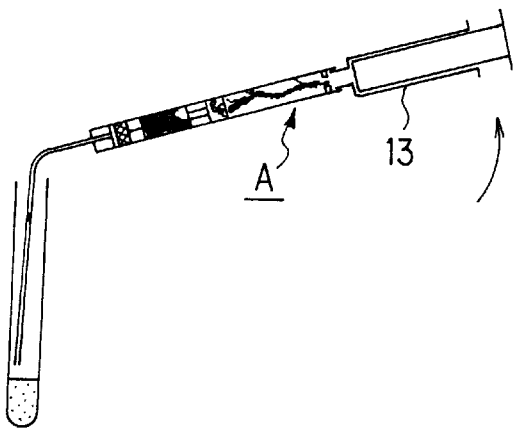
Figure 4B:
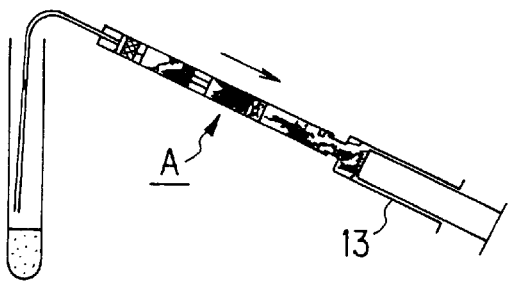

After the sampling tube 1 has been lifted from the sample solution, the plunger 14 of the syringe 13 is pulled to draw the sample into the filtering vessel A, or more specifically, into the area above the coloring composition 5 (or the area close to the sampling tube 1), as shown in FIG. 4(b).

Figure 4E:
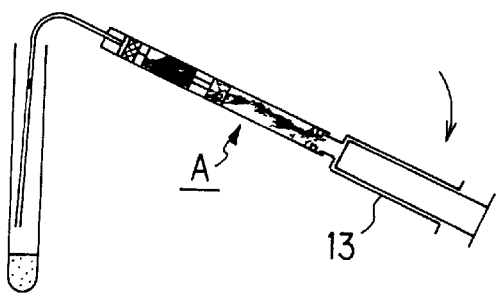
Figure 4C:
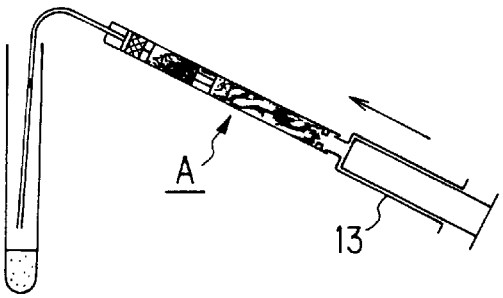

Then, the plunger 14 of the syringe 13 is pushed (to apply pressure) to push the coloring composition 5 back to its original position, as shown in FIG. 4(c). On this occasion, the air drawn in with the sample is forced out.

Then, the vessel is raised from its horizontal position at its end connected to the syringe 13 to move bubbles, as shown in FIG. 4(d), and thereafter lowered from its horizontal position to move the bubbles to their original position, as shown in FIG. 4(e). This movement of bubbles causes the sample and the coloring composition 5 to mix, whereby the sample is dyed. This step is usually taken at least once.

After the sample has been dyed as described, the piston 8 is moved in the aqueous solution 9 in the filtering vessel A for filtration, whereby the collection of the dyed bacteria on the hydrophobic filter 6 and the removal of any excess of coloring matter are carried out simultaneously.

The method of the first and second embodiment of the invention enables a simple operation, since it is possible to carry out the collection of the dyed bacteria on the hydrophobic filter and the removal of any excess of coloring matter simultaneously.

Figure 4F:
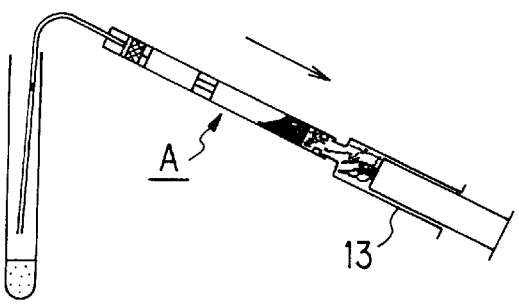

The step of filtration by the movement of the piston 8 in the aqueous solution 9 in the filtering vessel A is as shown in FIG. 4(f), and if the plunger 14 of the syringe 13 is pulled from the position shown in FIG. 4(e), the piston 8 moves in the aqueous solution 9 in the filtering vessel A, whereby a solution containing the dyed sample (a mixture of the sample solution and the coloring composition 5) is collected on the hydrophobic filter 6, while any excess of coloring matter is simultaneously removed.

After the collection of the dyed bacteria on the hydrophobic filter and the removal of any excess of coloring matter has been carried out simultaneously as described, the number of bacteria in the sample is determined from the degree of staining of the filter, as is the case with the first embodiment of the invention.

Description will now be made of the fifth, sixth, and seventh embodiments of the invention. The method of the fifth embodiment of the invention is preferably carried out by employing a kit of the sixth or seventh embodiments of the invention for determining the number of bacteria. Accordingly, the method of the fifth embodiment of the invention will be described with reference to the kit of the sixth and seventh embodiments of the invention.

When the method of the fifth embodiment of the invention is used for determining the number of bacteria in a sample, a sample containing bacteria (for example, fermented milk, or a fermented milk beverage) is drawn into a filtering vessel holding a hydrophobic filter for bacterial detection therein.

The filtering vessel duplicates that which has been described in connection with the first embodiment of the invention, etc. More specifically, the filtering vessel is tubular, or may be cylindrical or tubular, and may be of either plastics, such as vinyl chloride, or glass. Its capacity depends on the amount of the coloring composition, etc. as employed. The filtering vessel holds therein a hydrophobic filter for bacterial detection, and a support for the filter. The filtering vessel is preferably as described for the third, fourth or sixth embodiments of the invention.

Figure 5:
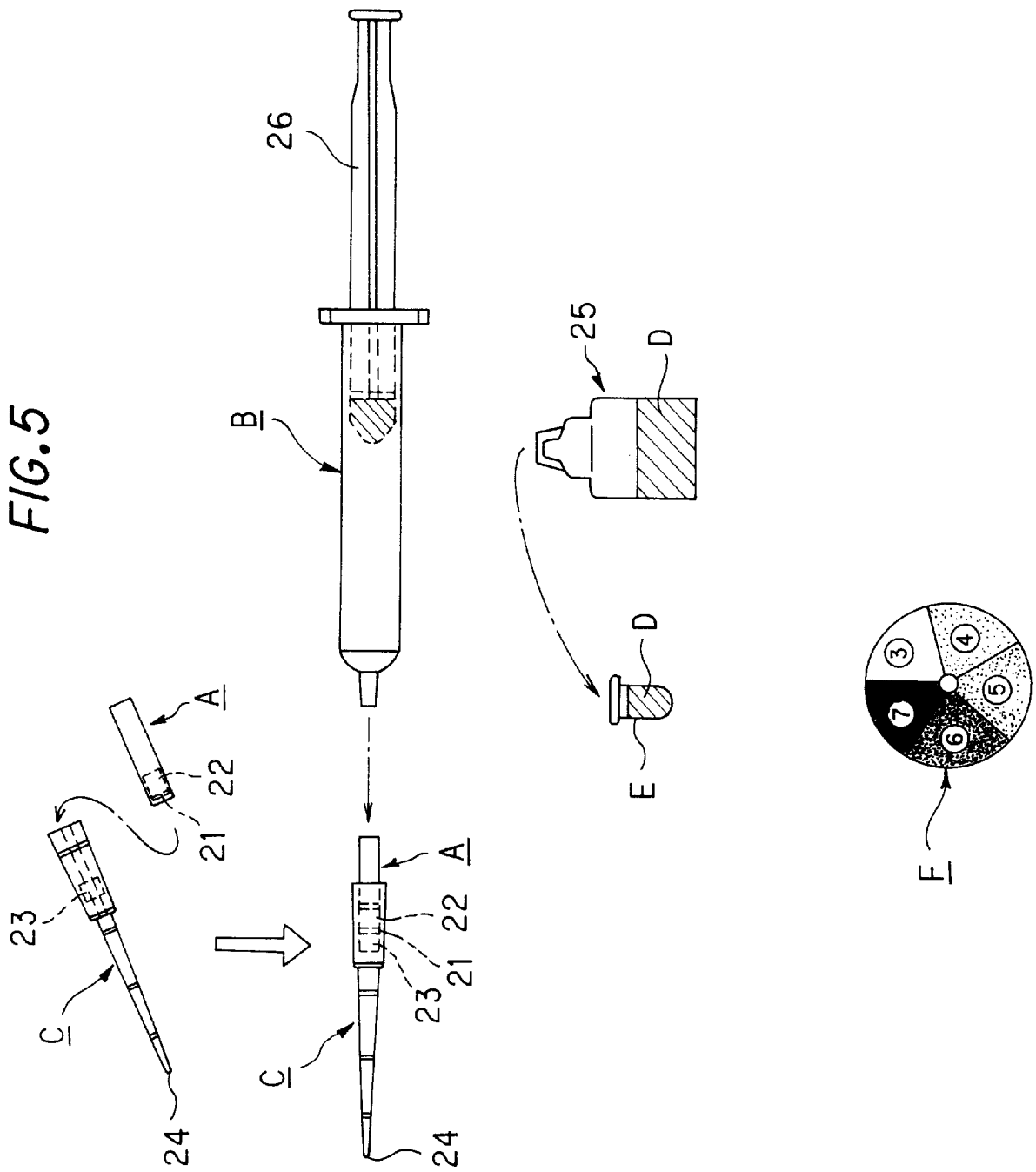
FIG. 5 is a schematic view showing one form of a kit of this invention for determining the number of bacteria in the sixth embodiment of the invention.
Figure 6:
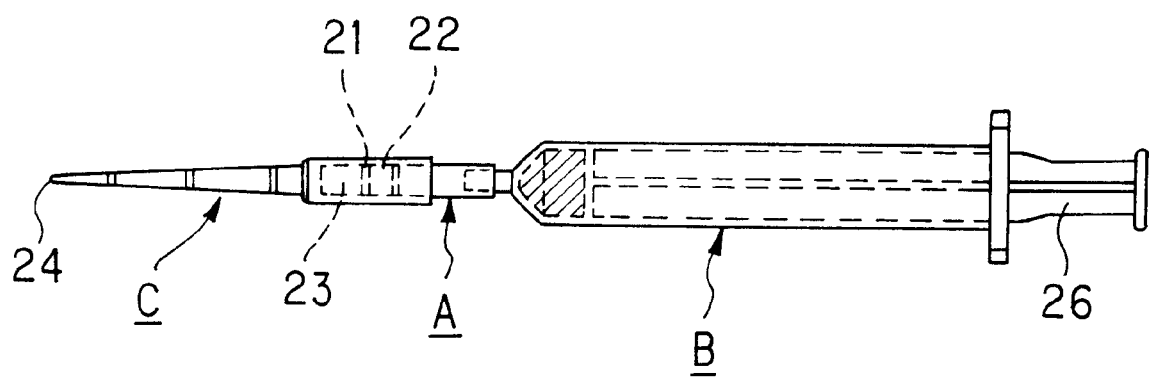
FIG. 6 is an explanatory view showing a combination of a kit of this invention for determining the number of bacteria in the sixth embodiment of the invention and a commercially available syringe which is ready for determining the number of bacteria.
Figure 6:
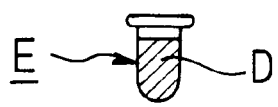
Figure 6:
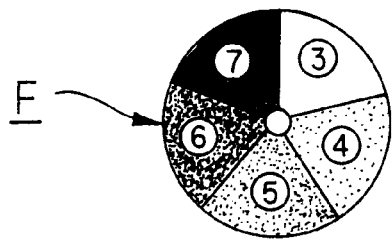

The fifth, sixth and seventh embodiments of the invention will now be described with reference to the drawings. FIG. 5 is a schematic view showing one form of a kit of the sixth embodiment of the invention for determining the number of bacteria. FIG. 6 is a schematic view of a combination of the kit of the sixth embodiment of the invention and a commercially available syringe which is ready for determining the number of bacteria. In the drawings, symbol A denotes a filtering vessel.

The filtering vessel A in the kit of the sixth embodiment of the invention holds a hydrophobic filter 21 for bacterial detection and a filter support 22 therein. The filtering vessel A is tubular, or may be cylindrical or tubular, and holds the hydrophobic filter 21 at one end thereof. The filtering vessel A may be of either plastics, such as vinyl chloride, or glass, but is preferably of plastics owing to its ease of handling.

The method of the fifth embodiment of the invention employs a hydrophobic filter 21 as a filter for bacterial detection. The hydrophobic filter 21 may be equal to the hydrophobic filter 6 as described in connection with the first embodiment of the invention (reference is made to the foregoing description for details on the hydrophobic filter, such as its material, pore diameter, and area of filtration under suction). The hydrophobic filter 21 is preferably made of polytetrafluoroethylene, or polypropylene, since it is easy to remove any excess of coloring material, as is the case with the first embodiment of the invention.

The filter support 22 may be of any material and shape if it can support the hydrophobic filter 21. It is usually formed from a silicone resin, or the like.

The other end of the filtering vessel A enables suction with a syringe B which can be attached to it at one end. The syringe B itself can be included in the kit of this invention, if required.

A sampling member C holding a prefilter 23 therein is detachably combined with the filtering vessel A at its end (at which it holds the hydrophobic filter 21), as shown in FIG. 5. The filtering vessel A and the sampling member C are usually so constructed that the filtering vessel A may fit at one end in the sampling member C and have its hydrophobic filter 21 contact the prefilter 23 in the sampling member C, as shown in FIGS. 5 and 6.

The sampling member C is tubular, or may be cylindrical or tubular, and has a tapered end provided with a sample inlet 24 through which it can take a sample. The sampling member C preferably has measuring graduations. FIG. 5 shows the sampling member C as having three graduations. The graduations may cover a range of 50 to 100 $\mu$l which is the amount of a sample which is usually employed.

The prefilter 23 in the sampling member C may be equal to the prefilter 4 as described in connection with the first embodiment of the invention. The prefilter 23 is used for removing animal cells, and if a sample containing bacteria contains also animal cells larger than bacteria, such as leukocytes, it does not pass any such animal cells, but collects them, while passing bacteria. The prefilter 23 can, therefore, be omitted, as is obvious from claim 18, if the sample is of, for example, fermented milk, or a fermented milk beverage, and is free from any such animal cells.

The prefilter 23 may have a pore diameter of, say, 6 to 60 $\mu$m. It is possible to use as the prefilter a polypropylene filter (having a pore diameter of, say, 7 $\mu$m), a urine sampling filter (made of vinyl chloride) for a medicine for a diagnosis for pregnancy, such as "Gonavislide" and "New Gonavislide" (products of Mochida Pharmaceutical Co., Ltd.) which will appear in the description of examples, a felt, or nonwoven fabric used in a commercially available oily-ink pen, or the like.

When the fifth embodiment of the is used for determining the number of bacteria in a sample, the sample (for example, fermented milk, or a fermented milk beverage) is first drawn by suction into the filtering vessel A holding the hydrophobic filter 21 for bacterial detection therein, and this step of suction will now be described.

The sampling member C holding the prefilter 23 therein is attached to (or fitted on) the end of the filtering vessel A (at which it holds the hydrophobic filter 21). They are so put together that the prefilter 23 may contact the hydrophobic filter 21. It is, however, alternatively possible to employ a sampling member C having no prefilter 23 as in the seventh embodiment of the invention.

Then, the syringe B is attached to the other end of the filtering vessel A (the opposite end thereof from the hydrophobic filter 21) to get ready for suction. These steps can, however, be reversed in order.

FIG. 6 shows the assembly which is ready for the step of suction. An appropriate amount of a sample containing bacteria is drawn by suction with the syringe B into the sampling member C through the sample inlet 24 at its distal end. The measuring graduations on the sampling member C provide a standard for the amount of the sample.

The samples to which the fifth embodiment of the invention are applicable include those listed above in the description of the first embodiment of the invention. More specifically, it is applicable to a wide variety of samples including not only urine, but also water-soluble metal processing fluids such as cutting, rolling and heat-treatment fluids, liquid foods such as liquid seasonings (soy, sauce, etc.), liquid foods and beverages (fermented milk, lactic-acid beverages, etc.) and alcoholic drinks (wine, sake, etc.), samples left after washing powdery, or solid foods (vegetables, fish, meat, etc.), water-soluble paints, and water, such as river, pond or hot-spring water, water in a water tank, or waste water from houses.

The method of the fifth embodiment of the invention is intended for determining quickly the total number of bacteria existing in any such sample, for example, *Escherichia coli*, *Staphylococcus aureus* and *Pseudomonas aeruginosa*.

The kit of the seventh embodiment of the invention is particularly useful for determining the number of bacteria in fermented milk and fermented-milk beverages quickly.

The sample which has been drawn in by suction with the syringe B as described above is extruded into a coloring composition D. The coloring composition D is held in an appropriate container (for example, a dropping bottle 25) forming a part of the kit, as shown in FIG. 5, and the kit further includes another appropriate container E capable of holding that amount of the coloring composition D which is necessary for about a single step of filtration by suction, for example, a microtube having a capacity of, say, 0.5 to 1.5 ml, so that it may hold the coloring composition D for actual use in determining the number of bacteria.

A small amount of coloring composition D is fed from the dropping bottle 25, or the like into the container E (such as a microtube), and the sample drawn into the syringe B is extruded for injection into the coloring composition, and is thoroughly mixed with it. As a result, the sample is dyed with the coloring composition D.

The coloring composition D is a composition which can be used for both dyeing and washing, and more specifically, it comprises coloring matter which can be used for dyeing bacteria, and water, or a buffer solution, and a surface active agent, if required.

Examples of the coloring matter which can be used for dyeing bacteria in accordance with the fifth embodiment of the invention include those listed above in the description of the first embodiment of the invention. Safranine, Fuchsine, Methylene Blue or Methyl Green is preferred from the standpoint of easy judgment, as is the case with the first embodiment of the invention.

The buffer solution which can be used has a pH of 4 to 9 and preferably has a pH of 5 to 7 to ensure the stability of the coloring matter. A preservative, such as ethanol, a surface active agent, etc. can be added, if required.

The concentration of the coloring matter is usually from 0.00001 to 0.00045% (w/v) and preferably from 0.00015 to 0.0004% (w/v) when it is Fuchsine. If its concentration is less than 0.00001%, it is insufficient for any satisfactory coloring, and if its concentration exceeds 0.00045%, it is difficult to remove any excess of the coloring matter.

If it is necessary to add a preservative, such as ethanol, it can be added in the amount of 0.1 to 15% (v/v). If a surface active agent is added, it can be added in the proportion of from 0.001 to 1.0% (w/v), and preferably from 0.01 to 0.6% (w/v).

The adequate amount of the coloring composition to be used per sample is two to five times the amount of the sample. The amount of each sample is usually 50 to 100 $\mu$l. Therefore, any sample in the amount of 100 $\mu$l requires 200 to 500 $\mu$l of coloring composition. No amount exceeding five times that of the sample is, however, required.

It is preferable for preventing any error to use the same amount of the coloring composition when preparing a color reference chart or a working curve as when applying it to any sample containing an unknown number of bacteria.

After the injection as stated above, the plunger 26 of the syringe B is immediately pulled to draw in the mixture of the coloring composition and the sample from the container E (such as a microtube) through the sample inlet 24 at the end of the sampling member C attached to the end of the syringe B, so that its filtration under suction may take place.

As a result of its filtration under suction, the dyed bacteria are collected on the hydrophobic filter 21. At the same time, any excess of coloring matter is removed. If the plunger 26 of the syringe B is pulled to produce suction, the solution containing the dyed sample (the mixed solution of the sample solution and the coloring composition D) is collected on the hydrophobic filter 21, while the excess of coloring matter is simultaneously removed.

The method of the fifth embodiment of the invention enables a simple process of operation, since it is possible to carry out the collection of the dyed bacteria on the hydrophobic filter and the removal of any excess of coloring matter simultaneously as stated above.

According to the method of the fifth embodiment of the invention, the collection of the dyed bacteria on the hydrophobic filter 21 and the removal of the excess of coloring matter are carried out simultaneously as stated above, and the number of bacteria in the sample is determined from the degree of staining of the filter 21.

After the collection of the dyed bacteria on the filter 21, the sampling member C is detached from the end of the syringe B to expose the end of the filtering vessel A. The degree of staining of the bacteria on the hydrophobic filter 21 held at the end of the filtering vessel A, or the intensity of their color is compared with, for example, a color reference chart F prepared by employing samples containing known numbers of bacteria, whereby the number of bacteria in the sample is determined. The color reference chart F shown in FIGS. 5 and 6 is merely an example, and each of the numbers (③ to ⑦) marked on the chart means "log number per ml".

According to the method of the fifth embodiment of the invention, the collection of the dyed bacteria on the hydrophobic filter and the removal of the excess of coloring matter are carried out simultaneously as stated above, and the number of bacteria in the sample is determined from the degree of staining of the filter.

The number of bacteria in the sample is determined from the degree of staining of the bacteria in the sample from which the excess of coloring matter has been removed, as stated above. For determining the number of bacteria, (1) visual comparison with the color reference chart is the simplest way, but (2) it is alternatively possible to employ calorimetric analysis based on the measurement of optical density (O.D.), as already stated in the description of the first embodiment of the invention. For details of these methods for determining the number of bacteria, reference is made to the description of the first embodiment of the invention.

The invention will now be described in detail by way of examples embodying it.

EXAMPLE 1

(1) Preparation of a color reference chart for determining the number of lactic-acid bacteria A commercially available yogurt (product manufactured and sold by Zen-No under the tradename: Grated Apple) was diluted with water to make dilutions containing lactic-acid bacteria in the amounts of ① about $10^5$/ml, ② about $10^6$/ml, and ③ about $10^7$/ml, respectively, and three standard samples were prepared from each dilution. The number of lactic-acid bacteria grown by culture was obtained by counting the number of lactic-acid bacteria grown by 72 hours of culture at 37° C. on a BCP added plate count agar culture medium (product of Eiken Chemical).

The device shown in FIG. 1 was used for experiments. The dimensions and reagents were as follows:

Filtering vessel A: 5 mm O.D., 4 mm I.D. and 135 mm long; made of vinyl chloride;

Coloring composition 5: 300 μl of a phosphoric acid buffer solution having a pH of 7, and containing 0.0002% of Fuchsine and 0.05% of Tween 20;

Hydrophobic filter 6 for bacterial detection: A polytetrafluoroethylene membrane filter (having a pore diameter of 3 μm and a coloring area diameter of 1.5 mm);

Filter support 7: A hollow plug formed from a silicone resin (4 mm O.D., 1.5 mm hole diameter, and 7 mm long).

Each standard sample in the amount of 100 μl was added to the coloring composition through the sample inlet, and the plunger 14 of the syringe 13 was pulled for filtration under suction. The collection of the dyed lactic-acid bacteria on the hydrophobic filter 6 and the removal of the excess of coloring matter were thereby carried out simultaneously. Visual examination was made of the degree of staining of lactic-acid bacteria on the hydrophobic filter 6 (or the degree of staining of circles having a diameter of 1.5 mm), and the results were as shown in Table 1 below.

TABLE 1

| Standard sample | Degree of staining | Judgment (number/ml) |
|---|---|---|
| ① | Weak (light pink) | About $10^5$/ml |

TABLE 1-continued

| Standard sample | Degree of staining | Judgment (number/ml) |
|---|---|---|
| ② | Medium (pink) | About $10^6$/ml |
| ③ | Strong (red) | $10^7$/ml or more |

Color photographs were taken of these stained filters as standard samples to prepare a color reference chart.

(2) Determination of the number of lactic-acid bacteria

The device as shown in FIG. 1 and used at (1) above was used for determining the number of lactic-acid bacteria in those samples of yogurt which had been stored in a refrigerator for two, three and four weeks, respectively. The dimensions of the device shown in FIG. 1 and the reagents used were as stated at (1) above.

Three kinds of yogurt (products manufactured and sold by Zen-No under the tradenames: Grated Apple, Plain Type, and Grated Carrot) which had been stored in the refrigerator for certain periods of time were each diluted with water to 1000 times as large in volume, and each diluted yogurt in the amount of 100 μl was added to the device as shown in FIG. 1 for filtration under suction. The collection of the dyed bacteria on the hydrophobic filter 6 and the removal of the excessive coloring matter were thereby carried out simultaneously. Visual examination was made of the degree of staining of lactic-acid bacteria on the hydrophobic filter 6 (or the degree of staining of circles having a diameter of 1.5 mm), and visual judgment was made by comparing the results with the color reference chart as prepared at (1) above.

The number of lactic-acid bacteria in each yogurt was determined by multiplying by 1000 ($10^3$) which was the number of times by which each yogurt had been diluted. Its determination took 60 seconds. The results are shown in Table 2.

For the sake of comparison, it also shows the number of lactic-acid bacteria as determined by culture (72 hours of culture at 37° C. on a BCP added plate count agar culture medium made by Eiken Chemical).

TABLE 2

| kind of yogurt | Method of determination | Number of lactic-acid bacteria (number/ml) | | |
|---|---|---|---|---|
| | | After 2 weeks of storage | After 3 weeks of storage | After 4 weeks of storage |
| Grated apple | This invention | $\geq 10^{10}$ | $10^9$ | $10^8$ |
| | Culture | $1.9 \times 10^{10}$ | $5.6 \times 10^8$ | $5.2 \times 10^8$ |
| Plain type | This invention | $\geq 10^{10}$ | $10^9$ | $10^8$ |
| | Culture | $4.1 \times 10^{10}$ | $8.1 \times 10^8$ | $9.3 \times 10^7$ |
| Grated carrot | This invention | $\geq 10^{10}$ | $10^9$ | $10^8$ |
| | Culture | $4.9 \times 10^{10}$ | $1.0 \times 10^9$ | $1.7 \times 10^8$ |

EXAMPLE 2

(1) Preparation of a color reference chart for determining the number of bacteria in urine

*Escherichia coli* (ATCC 11303) was used for experiments. The urine which had been collected from a healthy male, and to which 0.1% of glucose had been added, was subjected to sterile filtration by a polytetrafluoroethylene (PTFE) membrane filter (made by Toyo Filter Paper) having a pore diameter of 0.5 μm to prepare a culture medium.

The medium was inoculated with the colon bacilli, and left to stand at 37° C. for 24 hours of culture to form a cultured bacterial solution as a bacterial suspension for standard samples. The same urine of the healthy male was filtered by a polytetrafluoroethylene membrane filter (made by Toyo Filter Paper) having a pore diameter of 0.5 µm to prepare a bacterial diluent.

Appropriate amounts of bacterial diluent were added to the bacterial suspension for a standard sample to prepare five standard samples having bacterial concentrations of (①) about 1000/ml, ② about 10,000/ml, ③ about 100,000/ml, ④ about 1,000,000/ml, and ⑤ about 10,000,000/ml. The number of bacteria grown by culture was obtained by counting the number of colonies resulting from 24 hours of culture at 37° C. on a CLED agar plate culture medium.

The device shown in FIG. 2 was used for experiments. The dimensions and reagents were as follows:

Filtering vessel A: 5 mm O.D., 4 mm I.D. and 135 mm long; made of vinyl chloride;

Slender sampling tube 1: 2 mm O.D. and 1 mm I.D.; made of polyethylene;

Prefilter 4: 4 mm O.D. and 4 mm I.D.; made of polyvinyl alcohol, and having a pore diameter of 60 µm;

Coloring composition 5: 300 µl of a phosphoric acid buffer solution having a pH of 7, and containing 0.0002% of Fuchsine and 0.05% of Tween 20;

Hydrophobic filter 6 for bacterial detection: A polytetrafluoroethylene membrane filter (having a pore diameter of 3 µm and a coloring area diameter of 1.5 mm);

Filter support 7: A hollow plug formed from a silicone resin (4 mm O.D., 1.5 mm hole diameter, and 7 mm long);

Piston 8: Made of konjak (devil's-tongue), and 5 mm long;

Aqueous solution 9 drawn into the syringe: 800 µl of water.

The device was of such construction that the aqueous solution 9 was drawn into the syringe 13 under suction, and caused the piston 8 to move, whereby the dye composition 5 was filtered and the dyed bacteria were collected on the hydrophobic filter 6.

The standard sample (sample containing bacteria) was drawn into the sampling tube 1 up to the scale (100 µl), as shown in FIG. 2, and after the sampling tube 1 had been lifted from the sample, the sample therein was drawn into the filtering vessel A.

Then, the plunger 14 of the syringe 13 was pushed to push back the dye composition 5 to its original position As a result, the air which had been drawn in with the sample was forced out.

Then, the device was raised at the syringe 13 above its horizontal position to move bubbles, and was then lowered at the syringe 13 below its horizontal position to move the bubbles back to their original position. This movement of bubbles caused the dye composition 5 to mix with the sample and dye the bacteria.

Finally, the piston 8 was moved in the aqueous solution 9 in the filtering vessel A for filtration under suction with the syringe 13. This operation allowed the collection of the dyed bacteria on the hydrophobic filter 6 and the removal of the excessive coloring matter to occur simultaneously. Visual examination was made of the degree of staining of the bacteria on the hydrophobic filter 6 (or the degree of staining of circles having a diameter of 1.5 mm), and the results were as shown in Table 3 below.

TABLE 3

| Standard sample | Degree of staining | Judgment (number/ml) |
| --- | --- | --- |
| ① | Not stained | $\leq 10^3$ |
| ② | Very weak (very light pink) | About $10^4$ |
| ③ | Weak (light pink) | About $10^5$ |
| ④ | Medium (pink) | About $10^6$ |
| ⑤ | Strong (red) | $10^7 \leq$ |

Color photographs were taken of these stained filters as standard samples to prepare a color reference chart.

(2) Determination of the number of bacteria in urine

Samples of urine were collected from healthy persons and patients of various diseases, and the device as shown in FIG. 2 and used at (1) above was used for determining the number of bacteria in the urine of each person. The dimensions of the device as shown in FIG. 2 and the reagents used were as stated at (1) above.

The urine of each of the healthy persons and patients was drawn into the sampling tube 1 up to the scale (100 µl), as shown in FIG. 2, and after the sampling tube 1 had been lifted from the sample, the sample therein was drawn into the filtering vessel A.

Then, the plunger 14 of the syringe 13 was pushed to push back the dye composition 5 to its original position. As a result, the air which had been drawn in with the sample was forced out.

Then, the device was raised at the syringe 13 above its horizontal position to move bubbles, and was then lowered at the syringe 13 below its horizontal position to move the bubbles back to their original position. This movement of bubbles caused the dye composition 5 to mix with the sample and dye the bacteria.

Finally, the piston 8 was moved in the aqueous solution 9 in the filtering vessel A for filtration under suction with the syringe 13. This operation allowed the collection of the dyed bacteria on the hydrophobic filter 6 and the removal of the excessive coloring matter to occur simultaneously.

Visual examination was made of the degree of staining of the bacteria on the hydrophobic filter 6 (or the degree of staining of circles having a diameter of 1.5 mm), and visual judgment was made by comparing the results with the color reference chart as prepared at (1) above.

The determination took 60 seconds. The results are shown in Table 4. For the sake of comparison, it also shows the number of bacteria as grown on a CLED agar plate culture medium (by 24 hours of culture at 37° C.).

TABLE 4

| Urine sample | Judgment by the method of this invention (number/ml) | Number of bacteria as determined by culture on CLED agar plate (number/ml) |
| --- | --- | --- |
| Healthy person A (male, age 56) | $\leq 10^3$ | $5.0 \times 10^2$ |
| Healthy person B (female, age 52) | $\leq 10^3$ | $3.3 \times 10^3$ |
| Patient A (of an infection of the urinary tract, age unknown) | about $10^6$ | $2.3 \times 10^6$ |
| Patient B (of diabetes, age unknown) | about $10^5$ | $1.5 \times 10^5$ |
| Patient C (of an infection of the urinary tract, age unknown) | about $10^6$ | $1.0 \times 10^7$ |

TABLE 4-continued

| Urine sample | Judgment by the method of this invention (number/ml) | Number of bacteria as determined by culture on CLED agar plate (number/ml) |
|---|---|---|
| Patient D (of cerebral infarction, age unknown) | about $10^4$ | $14.8 \times 10^4$ |
| Patient E (of urethral homorrhage, age unknown) | about $10^5$ | $14.7 \times 10^5$ |

Comparative Example 1

When the number of bacteria in urine was determined by the method described in Japanese Patent Application Laid-Open No. Hei 4-218392, it took three minutes.

EXAMPLE 3

Examination was made of the degree of staining on a hydrophobic filter for bacterial detection when coloring matter was employed in different concentrations for samples containing equal numbers of bacteria.

Experiments were conducted as described below by employing *Escherichia coli* (ATCC 11303) as bacteria. A culture medium composed of a bouillon of meat was inoculated with bacteria, and left to stand at 37° C. for 24 hours for culture, and a bacterial diluent obtained by filtering the urine of a healthy male through a polytetrafluoroethylene membrane filter (made by Toyo Filter Paper) having a pore diameter of 0.5 µm was added to the cultured solution to prepare coloring solutions having bacterial concentrations of $10^4$/ml and $10^6$/ml.

Visual examination was made of the degree of staining on a hydrophobic filter for bacterial detection by employing a kit of this invention and coloring compositions containing 0.00001 to 0.0005% of coloring matter (Fuchsine). The degree of staining as visually determined was compared with the color reference chart as prepared in Example 2 (Table 3). The results are shown in Table 5.

TABLE 5

| concentration of coloring matter | Bacterial concentration of $10^4$/ml | | Bacterial concentration of $10^6$/ml | |
|---|---|---|---|---|
| | Degree of staining | Judgment (number/ml) | Degree of staining | Judgment (number/ml) |
| 0.0005% | Weak | $10^5$ | Strong | $10^7 \leq$ |
| 0.0004% | Very weak | $10^4$ | Medium | $10^6$ |
| 0.0003% | Very weak | $10^4$ | Medium | $10^6$ |
| 0.0002% | Very weak | $10^4$ | Medium | $10^6$ |
| 0.0001% | Very weak | $10^4$ | Medium | $10^6$ |
| 0.00005% | Very weak | $10^4$ | Medium | $10^6$ |
| 0.00001% | Very weak | $10^4$ | Weak | $10^5$ |

As is obvious from the results shown in Table 5, there was no coincidence between the degree of staining and the result of judgment when the coloring matter in the coloring composition had a concentration of 0.0005% or above, or below 0.00001%. It is also obvious from Table 5 that the preferred concentration of the coloring matter is in the range of 0.00015 to 0.0004%.

EXAMPLE 4

(1) Preparation of a color reference chart for determining the number of bacteria in urine Experiments were conducted as described below by employing *Escherichia coli* (ATCC 11303) and *Staphylococcus aureus* (IFO 3183) as bacteria.

A culture medium composed of a bouillon of meat was inoculated with bacteria, and left to stand at 37° C. for 24 hours to prepare a cultured solution as a bacterial suspension for standard samples. The urine of a healthy male was filtered by a polytetrafluoroethylene membrane filter (made by Toyo Filter Paper) having a pore diameter of 0.5 µm to prepare a bacterial diluent.

Appropriate amounts of bacterial diluent were added to the bacterial suspension for standard samples to prepare five standard samples having bacterial concentrations of ① about 1000/ml, ② about 10,000/ml, ③ about 100,000/ml, ④ about 1,000,000/ml, and ⑤ about 10,000,000/ml. The number of bacteria grown by culture was obtained by counting the number of colonies resulting from 24 hours of culture at 37° C. on a CLED agar plate culture medium.

The kit shown in FIGS. 5 and 6 was used for experiments. The dimensions and coloring composition were as follows:

Coloring composition D: A solution containing 0.0002% of Fuchsine, 0.85% of salt and 0.05% of Tween 20;

Filtering vessel A: A polypropylene tube having an O.D. of 4.6 mm, an I.D. of 4 mm and a length of 20 mm;

Sampling member C: A tip graduated for 10, 50 and 100 µl, and having an I.D. of 5 mm at its large end (product of Quality, U.S.A.);

Microtube (container E for the coloring composition): A polypropylene container having a capacity of 1.5 ml (product of Quality, U.S.A.);

Hydrophobic filter 21 for bacterial detection: A polytetrafluoroethylene membrane filter (having a pore diameter of 3 µm and a coloring area diameter of 1.5 mm);

Filter support 22: A silicone tube having a length of 7 mm (and an O.D. of 4 mm and an I.D. of 1.5 mm),;

Dropping bottle 25: A product of polypropylene having a capacity of 10 ml;

Prefilter 23: A product of polyvinyl alcohol having a diameter of 4 mm, a length of 4 mm and a pore diameter of 60 µm.

The syringe B having a capacity of 3 ml was attached to one end of the filtering vessel A, while the sampling member C holding the prefilter 23 therein was detachably fitted on the other end of the filtering vessel A (at which it had the hydrophobic filter 21 for bacterial detection), as shown in FIG. 6, and 100 µl of sample containing bacteria as stated above was introduced through the sample inlet 24 at the distal end of the sampling member C by suction with the syringe B.

After the introduction of the sample by suction with the syringe B as stated above, it was forced out and injected into the container E (microtube) holding 350 µl (7 or 8 droplets) of coloring composition D therein.

After its injection, the plunger 26 of the syringe was immediately pulled to draw in for filtration the mixture of the coloring composition and the sample from the container E (microtube) through the sample inlet 24 at the distal end of the sampling member C attached to the end of the syringe B. This step of filtration under suction caused the collection of the dyed bacteria on the hydrophobic filter 21 and the removal of the excessive coloring matter to take place simultaneously.

After the collection of the dyed bacteria on the hydrophobic filter 21 as stated, the sampling member C was detached from the end of the syringe B to expose the end of the filtering vessel A, and visual examination was made of the degree of staining of the bacteria on the hydrophobic filter 21 at the end of the filtering vessel A, and the results were as shown in Table 6 below.

TABLE 6

| Standard sample | Degree of staining and judgment | | | |
|---|---|---|---|---|
| | *Escherichia coli* | Judgment (number/ml) | *Staphylococcus aureus* | Judgment (number/ml) |
| ① | None | $\leq 10^3$ | None | $\leq 10^3$ |
| ② | Very weak | about $10^4$ | Very weak | about $10^4$ |
| ③ | Weak | about $10^5$ | Weak | about $10^5$ |
| ④ | Somewhat strong | about $10^6$ | Somewhat strong | about $10^6$ |
| ⑤ | Strong | about $10^7$ | Strong | about $10^7$ |
| No bacteria added | None | — | None | — |

Color photographs were taken of these stained filters as standard samples to prepare a color reference chart. There was no substantial difference in the degree of staining between *Escherichia coli* and *Staphylococcus aureus*.

(2) Determination of the number of bacteria in urine

The process as described at (1) above for the preparation of a color reference chart for determining the number of bacteria in urine was repeated on samples of urine of healthy persons and patients of various diseases and visual judgment was made by comparing the results with the color reference chart as prepared at (1) above to determine the number of bacteria in each urine sample. The results are shown in Table 7.

For the sake of comparison, the table also shows the number of bacteria as determined by 24 hours of culture at 37° C. on a CLED agar plate culture medium.

TABLE 7

| Urine sample | Judgment by the method of this invention (number/ml) | Number of bacteria as determined by culture on CLED agar plate (number/ml) |
|---|---|---|
| Healthy person A (male, age 56) | $\leq 10^3$ | $1.7 \times 10^3$ |
| Healthy person B (female, age 52) | $\leq 10^3$ | $3.0 \times 10^3$ |
| Patient A (of an infection of the urinary tract, age and sex unknown) | $10^7$ | $6.8 \times 10^7$ |
| Patient B (of an infection of the urinary tract, age and sex unknown) | $10^5$ | $4.2 \times 10^5$ |
| Patient C (of liver cancer, age and sex unknown) | $10^4$ | $3.2 \times 10^4$ |
| Patient D (of cystitis, female, age 53) | $10^6$ | $2.0 \times 10^6$ |

EXAMPLE 5

(1) Preparation of a color reference chart for determining the number of bacteria in a fermented milk beverage A commercially available yogurt (product manufactured and sold by Zen-No under the tradename: "GRATED APPLE") was diluted with water to make dilutions containing bacteria in the amounts of ① about $10^5$/ml, ② about $10^6$/ml, and ③ about $10^7$/ml, respectively, and three standard samples were prepared from each dilution. The number of bacteria as determined by culture was obtained by counting the number of colonies grown by 72 hours of culture at 37° C. on a BCP added plate count agar culture medium (product of Eiken Chemical).

The kit as used in Example 4, but excluding the prefilter was employed for determining the number of bacteria, and the reagents, devices, and operation were as described in Example 4.

The process of Example 4 was repeated for dyeing 100 μl of each standard sample and filtering it under suction, and visual examination was made of the degree of staining of the bacteria on the hydrophobic filter 21, and gave the results as shown in Table 8 below.

TABLE 8

| Standard sample | Degree of staining | Judgment (number/ml) |
|---|---|---|
| (1) | Weak (light pink) | About $10^5$/ml |
| (2) | Somewhat strong (pink) | About $10^6$/ml |
| (3) | Strong (red) | About $10^7$/ml |

Color photographs were taken of these stained filters as standard samples to prepare a color reference chart.

(2) Determination of the number of bacteria in fermented milk beverages

Three kinds of yogurt (products manufactured and sold by Zen-No under the tradenames: "GRATED APPLE", "PLAIN TYPE", and "GRATED CARROT") which had been stored in a refrigerator for certain periods of time were each diluted with water to 1000 times as large in volume to prepare samples.

The process as described above at (1) for the standard samples was repeated for dyeing 100 μl of each sample and filtering it under suction. As a result, the collection of the dyed bacteria on the hydrophobic filter 21 and the removal of the excessive coloring matter were carried out simultaneously. Visual examination was made of the degree of staining of the bacteria on the filter 21, and visual judgment was made by comparing the results with the color reference chart as prepared at (1) above.

The number of bacteria in each yogurt was determined by multiplying the results by 1000 ($10^3$) which was the number of times by which each yogurt had been diluted. Its determination took 60 seconds. The results are shown in Table 9.

For the sake of comparison, the table also shows the number of bacteria as determined by culture (72 hours of culture at 37° C. on a BCP added plate count agar culture medium made by Eiken Chemical).

TABLE 9

| Kind of yogurt | Method of determination | Number of bacteria (number/ml) | | | |
|---|---|---|---|---|---|
| | | Initial | After 2 weeks of storage | After 3 weeks of storage | After 4 weeks of storage |
| Grated Apple | This invention | $\geq 10^{10}$ | $\geq 10^{10}$ | $10^9$ | $10^8$ |
| | Culture | $3.0 \times 10^{10}$ | $1.9 \times 10^{10}$ | $5.6 \times 10^8$ | $5.2 \times 10^8$ |
| Plain Type | This invention | $\geq 10^{10}$ | $\geq 10^{10}$ | $10^9$ | $10^8$ |
| | Culture | $6.5 \times 10^{10}$ | $4.1 \times 10^8$ | $8.1 \times 10^8$ | $9.3 \times 10^7$ |
| Grated Carrot | This invention | $\geq 10^{10}$ | $\geq 10^{10}$ | $10^9$ | $10^8$ |
| | Culture | $8.0 \times 10^{10}$ | $4.9 \times 10^{10}$ | $1.0 \times 10^9$ | $1.7 \times 10^8$ |

The methods of the first and third embodiments of the invention make it possible to carry out the collection of dyed bacteria on a hydrophobic filter and the removal of any excessive coloring matter simultaneously in a single step of filtering operation and thereby determine the number of bacteria in a sample quickly and easily. The methods of the first and third embodiments of the invention make it possible to obtain results usually within one minute (in about 30 seconds after experience has been gained), and the method of the first embodiment of the invention enables a particularly quick determination.

The methods of the first and third embodiments of the invention make it possible to determine the number of bacteria in a sample without requiring any expert skill, or knowledge.

Moreover, the methods of the first and third embodiments of the invention make it possible to check the presence of bacteria without relying upon culture, and can, therefore, be utilized for the screening of samples for a bacteriological examination in a hospital to thereby reduce the relevant costs of the patients and hospital.

The methods of the first and third embodiments of the invention can be carried out even in a small hospital, or clinic, or even by any ordinary person, since they do not require any special apparatus.

Moreover, the methods of the first and third embodiments of the invention have a very wide scope of use, since they are applicable to many kinds of bacteria if a hydrophobic filter having an appropriate pore diameter is employed.

The devices of the second and fourth embodiments of the invention for determining the number of bacteria enable a very simple process which does not involve any such work as taking a sample by a dropper, or dropping a reagent from a reagent bottle, but for which it is sufficient to use a syringe for filtration. They do not require any skill, or any special equipment, but enable determination to be carried out at any place.

The device of the fourth embodiment of the invention is a disposable one of simple construction, but enables the reuse of a syringe, since it ensures that no sample enter the syringe and cause its bacterial, or like contamination. The device of the third embodiment of the invention is intended mainly for determining the number of lactic-acid bacteria, and enables the reuse of a syringe, since it is unlikely to bring about any serious problem of bacterial contamination.

The devices of the second and fourth embodiments of the invention can advantageously be used at any site, since they are very simple, and inexpensive, and do not require any special apparatus. It is particularly beneficial that any ordinary person, or layman can use the device easily to inspect the quality of any water in his environment, such as river, pond, sea or hot-spring water, and thereby contribute to the preservation of a sound environment, and also to even examine the number of bacteria in liquid or solid, or other food.

Moreover, the devices of the second and fourth embodiments of the invention can be used as a container for transporting to an examination room any sample containing bacteria to be identified after their quantitative analysis, if the slender tube is closed by heating, or otherwise, as the sample can be held in the device under suction.

The second and fourth embodiments of the invention can be said to be somewhat more complicated than the first and fourth embodiments, which are very simple, since they are intended for enabling the reuse of a syringe without giving rise to any recently controversial problem, such as bacterial contamination.

The method of the fifth embodiment of the invention can determine the number of bacteria in a sample quickly and easily, since it does not require any dropper, or like device for taking a sample, but can carry out the collection of dyed bacteria on a hydrophobic filter and the removal of any excessive coloring matter simultaneously in a single step of filtering operation under suction with a syringe. The method of the fifth embodiment of the invention makes it possible to obtain results usually within one minute (and in about 30 seconds after experience has been gained).

The method of the fifth embodiment of the invention makes it possible to determine the number of bacteria in a sample without requiring any expert skill, or knowledge.

Moreover, the method of the fifth embodiment of the invention makes it possible to check the presence of bacteria without relying upon culture, and can, therefore, be utilized for the screening of samples for a bacteriological examination in a hospital to thereby reduce the relevant costs of the patients and hospital.

The method of the fifth embodiment of the invention can be carried out even in a small hospital, or clinic, or even by any ordinary person, since they do not require any special apparatus.

The method of the fifth embodiment of the invention has a very wide scope of use, since it is applicable to many kinds of bacteria if a hydrophobic filter having an adequate pore diameter is employed.

The method of the fifth embodiment of the invention contributes to the proper control of food quality, since it makes it possible to ascertain the number of bacteria in food (such as yogurt) before its shipment.

The kits of the sixth and seventh embodiments of the invention for determining the number of bacteria enable a very simple process which does not involve any such work as taking a sample by a dropper, or dropping a reagent from a reagent bottle, but for which it is sufficient to use a syringe for filtration. They do not require any skill, or any special equipment, but enable determination to be carried out at any place.

The kits of the sixth and seventh embodiments of the invention set forth in claims 17 and 18 can advantageously be used at any site, since they are very simple, and inexpensive, and do not require any special apparatus. It is particularly beneficial that any ordinary person, or layman can use the kits easily to inspect the quality of any water in his environment, such as river, pond, sea or hot-spring water, and thereby contribute to the preservation of a sound environment, and also to even examine the number of bacteria in liquid or solid, or other food.

Moreover, the kits of the sixth and seventh embodiments of the invention can be used as a container for transporting to an examination room any sample containing bacteria to be identified after their quantitative analysis, if the slender tube is closed by heating, or otherwise, as the sample can be held in the device under suction.

Posibility of Industrial Utilization

This invention can, thus, be used for examination in a wide variety of fields including urine analysis (for diagnosis) and metal processing.

We claim:

1. A method of determining the number of bacteria in a sample which comprises:
   (a) introducing a sample containing bacteria into a tubular filtering vessel holding therein (i) a hydrophobic filter for bacterial detection, (ii) a coloring composition disposed on a side of said filter where the sample is introduced into said vessel, and (iii) a support for said filter disposed on the opposite side of said hydrophobic filter from said coloring composition,
   (b) dyeing the bacteria,
   (c) filtering the sample in a single step by suction from said support to collect the dyed bacteria on said hydrophobic filter and to remove an excess of coloring matter, and (d) determining the number of the bacteria in the sample from the degree of staining of said hydrophobic filter.

2. A method of determining the number of bacteria in a sample which comprises:
   (a) introducing a sample containing bacteria into a tubular filtering vessel holding therein (i) a hydrophobic filter for bacterial detection, (ii) a coloring composition on a side of said filter where the sample is introduced, (iii) a support for said hydrophobic filter, (iv) a piston and (v) an aqueous solution disposed on the opposite side of said hydrophobic filter from said coloring composition,
   (b) dyeing the bacteria,
   (c) filtering the sample in a single step by moving said piston in said aqueous solution to cause a suction, to collect the dyed bacteria on said hydrophobic filter and to remove an excess of coloring matter, and
   (d) determining the number of the bacteria in the sample from the degree of staining of said hydrophobic filter.

3. The method as set forth in claim 1, wherein said sample is fermented milk, or a lactic-acid beverage.

4. The method as set forth in claim 2, wherein said sample is urine.

5. The method as set forth in claim 1 or 2, wherein said composition comprises coloring matter, a buffer solution and a surface active agent.

6. The method as set forth in claim 1 or 2, wherein said composition contains coloring matter at a concentration of 0.00001 to 0.00045% (w/v).

7. The method as set forth in claim 1, 2 or 6, wherein said composition contains a surface active agent at a concentration of 0.001 to 1.0% (w/v).

8. A device for determining the number of bacteria which comprises a tubular filtering vessel having a sample inlet at one end, while the other end thereof enables suction with a syringe, said vessel holding a coloring composition, a hydrophobic filter for bacterial detection and a filter support disposed therein in their order as viewed from said sample inlet.

9. A device for determining the number of bacteria which comprises a tubular filtering vessel having a slender sampling tube connected at one end, while the other end thereof enables suction with a syringe, said vessel holding a prefilter, a coloring composition, a hydrophobic filter for bacterial detection, a filter support, a piston movable in said vessel, an aqueous solution and a plug preventing the leakage of said aqueous solution disposed therein in their order as viewed from said slender tube.

10. A method of determining the number of bacteria in a sample which comprises:
    (a) introducing a sample containing bacteria by suction into a filtering vessel holding a hydrophobic filter for bacterial detection and a filter support therein through a sampling member fitted at an end of said filtering vessel,
    (b) extruding the sample into a container containing a coloring composition,
    (c) filtering the sample in a single step by suction to collect the dyed bacteria on said hydrophobic filter and
    (d) determining the number of the bacteria in the sample from the degree of staining of said hydrophobic filter.

11. The method as set forth in claim 10, wherein said composition comprises coloring matter, a buffer solution and a surface active agent.

12. The method as set forth in claim 10, wherein said composition contains coloring matter at a concentration of 0.00001 to 0.00045% (w/v).

13. The method as set forth in claim 10 or 12, wherein said composition contains a surface active agent at a concentration of 0.001 to 1.0% (w/v).

14. The method as set forth in claim 10, wherein said vessel has one end to which a sampling member holding a prefilter therein is attached.

15. The method as set forth in any of claims 10 to 14, wherein said sample is of urine.

16. The method as set forth in claim 10, wherein said sample is of fermented milk, or a fermented milk beverage.

17. A kit for determining the number of bacteria in the method of claim 10 which comprises a filtering vessel holding a hydrophobic filter for bacterial detection and a filter support therein, a sampling member containing a prefilter and adapted for connection to one end of said vessel, a coloring composition, a container for said composition, and a color reference chart.

18. A kit for determining the number of bacteria in the method of claim 10 which comprises a filtering vessel holding a hydrophobic filter for bacterial detection and a filter support therein, a sampling member adapted for connection to one end of said vessel, a coloring composition, a container for said composition, and a color reference chart.

19. The method as set forth in claim 2, wherein said composition comprises coloring matter, a buffer solution and a surface active agent.

20. The method as set forth in claim 2, wherein said composition contains coloring matter at a concentration of 0.00001 to 0.00045% (w/v).

21. A method as set forth in claim 2, wherein said composition contains a surface active agent at a concentration of 0.001 to 1.0% (w/v).

22. A method as set forth in claim 6, wherein said composition contains a surface active agent at a concentration of 0.001 to 1.0% (w/v).

23. A method as set forth in claim 20, wherein said composition contains a surface active agent at a concentration of 0.001 to 1.0% (w/v).

24. A method as set forth in claim 12, wherein said composition contains a surface active agent at a concentration of 0.001 to 1.0% (w/v).

25. A method as set forth in claim 11, wherein said sample is of urine.

26. A method as set forth in claim 12, wherein said sample is of urine.

27. A method as set forth in claim 13, wherein said sample is of urine.

28. A method as set forth in claim 14, wherein said sample is of urine.

29. A method as set forth in claim 24, wherein said sample is of urine.

* * * * *